(12) United States Patent
Miller et al.

(10) Patent No.: US 8,004,021 B2
(45) Date of Patent: Aug. 23, 2011

(54) MICROFABRICATED DEVICES AND METHOD FOR FABRICATING MICROFABRICATED DEVICES

(75) Inventors: Michael F. Miller, Hollis, NH (US); Shivalik Bakshi, Boston, MA (US)

(73) Assignee: BioScale, Inc., Lexington, MA (US)

( * ) Notice: Subject to any disclaimer, the term of this patent is extended or adjusted under 35 U.S.C. 154(b) by 0 days.

(21) Appl. No.: 11/736,168

(22) Filed: Apr. 17, 2007

(65) Prior Publication Data

US 2007/0284699 A1    Dec. 13, 2007

Related U.S. Application Data

(60) Provisional application No. 60/793,848, filed on Apr. 21, 2006.

(51) Int. Cl.
*H01L 27/148* (2006.01)

(52) U.S. Cl. .................. 257/226; 438/283

(58) Field of Classification Search .......... 257/226, 257/232; 73/24.06, 54.41, 61.75; 436/283.1, 436/267.1; 438/287.2
See application file for complete search history.

(56) References Cited

U.S. PATENT DOCUMENTS

| | | | |
|---|---|---|---|
| 4,278,492 A | 7/1981 | Cross et al. | 156/627 |
| 5,129,262 A | 7/1992 | White et al. | 73/599 |
| 5,189,914 A | 3/1993 | White et al. | 73/599 |
| 5,454,904 A | 10/1995 | Ghezzo et al. | 216/13 |
| 5,490,034 A | 2/1996 | Zavracky et al. | 361/283.4 |
| 5,501,893 A | 3/1996 | Laermer et al. | 428/161 |
| 5,565,625 A | 10/1996 | Howe et al. | 73/514.16 |
| 5,605,598 A | 2/1997 | Greiff | 156/630.1 |
| 5,668,303 A * | 9/1997 | Giesler et al. | 73/24.06 |
| 5,725,729 A | 3/1998 | Greiff | 156/657.1 |
| 5,760,305 A | 6/1998 | Greiff | 73/514.15 |
| 5,836,203 A | 11/1998 | Martin et al. | 73/579 |
| 5,932,953 A * | 8/1999 | Drees et al. | 310/324 |
| 5,969,250 A | 10/1999 | Greiff | 73/514.38 |
| 6,091,182 A | 7/2000 | Takeuchi et al. | 310/330 |
| 6,192,757 B1 | 2/2001 | Tsang et al. | 73/514.32 |
| 6,223,598 B1 | 5/2001 | Judy | 73/514.32 |
| 6,257,059 B1 | 7/2001 | Weinberg et al. | 73/504.16 |
| 6,323,580 B1 | 11/2001 | Bernstein | 310/324 |
| 6,388,789 B1 | 5/2002 | Bernstein | 359/198 |

(Continued)

FOREIGN PATENT DOCUMENTS

EP    1752663    2/2007

(Continued)

OTHER PUBLICATIONS

Grate, et al., "Acoustic Wave Sensors," Sensors Update, 1996, pp. 37-83.

(Continued)

*Primary Examiner* — Howard Weiss
*Assistant Examiner* — Steven H Rao
(74) *Attorney, Agent, or Firm* — Proskauer Rose LLP

(57) ABSTRACT

Microfabricated devices for operation in a fluid that include a substrate that has a first and second surface and a first electrode material layer located over the first surface of the substrate. The devices have a piezoelectric material layer located over the first electrode material layer and a second electrode material layer located over the piezoelectric material layer. The devices also include a layer of isolation material located over the second electrode material layer that at least one of chemically or electrically isolates a portion of the second electrode material layer from a fluid. Some devices include a layer of conductive material located over the layer of isolation material.

19 Claims, 8 Drawing Sheets

U.S. PATENT DOCUMENTS

| | | | |
|---|---|---|---|
| 6,433,401 B1 | 8/2002 | Clark et al. | 257/524 |
| 6,455,980 B1 | 9/2002 | Bernstein | 310/324 |
| 6,457,361 B1 | 10/2002 | Takeuchi et al. | 73/580 |
| 6,506,620 B1 | 1/2003 | Scharf et al. | 438/52 |
| 6,511,915 B2 | 1/2003 | Mlcak | 438/695 |
| 6,577,043 B2 * | 6/2003 | Tsukai et al. | 310/320 |
| 6,673,694 B2 | 1/2004 | Borenstein | 438/411 |
| 6,688,158 B2 | 2/2004 | Cunningham et al. | 73/24.06 |
| 6,777,727 B2 * | 8/2004 | Dunn et al. | 257/257 |
| 6,778,908 B2 | 8/2004 | Martorana et al. | 702/9 |
| 6,790,775 B2 | 9/2004 | Fartash | 438/667 |
| 6,837,097 B2 | 1/2005 | Cunningham et al. | 73/24.06 |
| 6,851,297 B2 | 2/2005 | Cunningham et al. | 73/24.06 |
| 6,887,391 B1 | 5/2005 | Daneman et al. | 216/2 |
| 6,946,314 B2 | 9/2005 | Sawyer et al. | 438/50 |
| 7,000,453 B2 | 2/2006 | Cunningham et al. | 73/24.06 |
| 7,109,633 B2 | 9/2006 | Weinberg et al. | 310/313 B |
| 7,118,922 B1 | 10/2006 | Bhansali et al. | 436/518 |
| 7,410,811 B2 | 8/2008 | Lin et al. | 436/526 |
| 2002/0067106 A1 | 6/2002 | Sunwoo et al. | 310/330 |
| 2002/0115198 A1 * | 8/2002 | Nerenberg et al. | 435/287.2 |
| 2003/0010745 A1 | 1/2003 | Field | 216/2 |
| 2003/0012693 A1 | 1/2003 | Otillar et al. | 422/58 |
| 2003/0020367 A1 | 1/2003 | Maeda et al. | 310/313 D |
| 2003/0119220 A1 | 6/2003 | Mlcak et al. | 438/52 |
| 2003/0154031 A1 | 8/2003 | Potyrailo et al. | 702/19 |
| 2003/0194710 A1 | 10/2003 | Yang | 435/6 |
| 2004/0038195 A1 | 2/2004 | Nerenberg et al. | 435/4 |
| 2004/0043615 A1 | 3/2004 | Yamamoto et al. | 438/689 |
| 2004/0065638 A1 | 4/2004 | Gogoi | 216/2 |
| 2004/0159629 A1 | 8/2004 | Busta | 216/22 |
| 2004/0175300 A1 | 9/2004 | Indermuhle et al. | 422/102 |
| 2004/0197931 A1 | 10/2004 | Indermuhle et al. | 436/514 |
| 2005/0014306 A1 | 1/2005 | Yao et al. | 438/52 |
| 2005/0045276 A1 | 3/2005 | Patel et al. | 156/345.43 |
| 2005/0064619 A1 | 3/2005 | Chavan et al. | 438/52 |
| 2005/0148147 A1 | 7/2005 | Keating et al. | 438/299 |
| 2006/0286685 A1 | 12/2006 | Miller et al. | 436/526 |

FOREIGN PATENT DOCUMENTS

| | | |
|---|---|---|
| WO | WO 2005/111426 | 11/2005 |

OTHER PUBLICATIONS

*The RF and Microwave Handbook*, Chapter 6, "Passive Technologies," Sections 6.1-6.5, CRC Press LLC, 2001, pp. 6-2-6-83.
R. M. White, "Direct Piezoelectric Coupling to Surface Elastic Waves," Applied Physics Letters, vol. 7 (Dec. 15, 1965), pp. 314-316.
J. F. Dias et al., "Frequency/Stress Sensitivity of S.A.W. Resonators," Electronics Letters, vol. 12, No. 22, Oct. 1976, pp. 580-582.
S. W. Wenzel, "Applications of Ultrasonic Lamb Waves," dissertation submitted in partial satisfaction of the requirements for the degree of Doctor of Philosophy in Engineering/Electrical Engineering and Computer Sciences, University of California at Davis (1992).
J. Neumeister et al., "A SAW Delay-line Oscillator as a High-resolution Temperature Sensor," Sensors and Actuators, (Mar. 1990), pp. 670-672.
W. C. Tang, "Electrostatic Comb Drive for Resonant Sensor and Actuator Applications," Ph.D. Thesis, Electrical Engineering and Computer Sciences, University of California Berkeley, Berkeley, CA, Nov. 1990.
R. L. Baer et al., "Phase Noise Measurements of Flexural Plate Wave Ultrasonic Sensors," 1991 IEEE Ultrasonics Symposium, 1991, pp. 321-326.
J. W. Grate et al., "Flexural Plate Wave Devices for Chemical Analysis," Analytical Chemistry, vol. 63, 1991, pp. 1552-1561.
Gianchandani et al., "A Bulk Silicon Dissolved Wafer Process for Microelectromechanical Devices," Journal of Microelectromechanical Systems, vol. 1, No. 2, Jun. 1992, pp. 77-85.
J. W. Grate et al., "Frequency-Independent and Frequency-Dependent Polymer Transitions Observed on Flexural Plate Wave Ultrasonic Sensors," Analytical Chemistry, vol. 64, 1992, pp. 413-423.
Giesler et al., "Electrostatic excitation and capacitive detection of flexural plate-waves," Sensors and Actuators A, vol. 36, 1993, pp. 113-119.
J. W. Grate et al., "Acoustic Wave Microsensors—Part I" Analytical Chemistry, vol. 65, No. 21, Nov. 1, 1993, pp. 940A-948A.
J. W. Grate et al., "Acoustic Wave Microsensors—Part II" Analytical Chemistry, vol. 65, No. 22, Nov. 15, 1993, pp. 987A-996A.
J. W. Grate et al., "Smart Sensor System for Trace Organophosphorus and Organosulfur Vapor Detection Employing a Temperature-Controlled Array of Surface Acoustic Wave Sensors, Automated Sample Preconcentration, and Pattern Recognition," Analytical Chemistry, vol. 65, No. 14, Jul. 15, 1993, pp. 1868-1881.
E.H. Yang et al., Sensors and Actuators—Fabrication and dynamic testing of electrostatic actuators with p + silicon diaphragms, vol. 50 (1995), pp. 151-156.
K. R. Williams, et al., "Etch Rates for Micromachining Processing," Journal of Microelectromechanical Systems, vol. 5, No. 4, Dec. 1996, pp. 256-269.
A. F. Collings et al., "Biosensors: recent advances," Rep. Prog. Phys., vol. 60, 1997, pp. 1397-1445.
R. M. White, "Introductory Lecture—Acoustic interactions from Faraday's crispations to MEMS," Faraday Discuss, vol. 107 (1997), pp. 1-13.
D. S. Ballantine, Jr. et al., "Acoustic Wave Sensors—*Theory, Design, and Physico-Chemical Applications*," Academic Press, New York, 1997.
J. C. Pyun et al., "Development of a biosensor for *E. coli* based on a flexural plate wave (FPW) transducer," Biosensors & Bioelectronics, vol. 13, 1998, pp. 839-845.
N. Yazdi et al., "Micromachined Inertial Sensors," Proceedings of the IEEE, vol. 86, No. 8, Aug. 1998, pp. 1640-1659.
A. W. Wang et al., "A Silicon-based Immunoassay for Detection of Breast Cancer Antigens," Sensors and Actuators B, vol. 49 (1998), pp. 13-21.
S. E. Cowan et al., "Ultrasonic Flexural-Plate-Wave Sensor for Detecting the Concentration of Settling *E. coli* W3110 Cells," Analytical Chemistry, vol. 71, No. 16, Aug. 15, 1999, pp. 3622-3625.
A. Janshoff et al., "Piezoelectric Mass-Sensing Devices as Biosensors—An Alternative to Optical Biosensors?," Angew. Chem. Int. Ed., vol. 39, 2000, pp. 4005-4032.
J. Choi et al., "A new magnetic bead-based, filterless bio-separator with planar electromagnet surfaces for integrated bio-detection systems," Sensors and Actuators B, vol. 68, 2000, pp. 34-39.
M. S. Weinberg et al., "Modeling Flexural Plate Wave Devices," Journal of Microelectromechanical Systems, vol. 9, No. 3. (Sep. 2000), pp. 370-379.
B. Cunningham et al., "Design, fabrication and vapor characterization of a microfabricated flexural plate resonator sensor and application to integrated sensor arrays," Sensors and Actuators B, vol. 73, 2001, pp. 112-123.
K. M. Lakin, "Thin Film Resonators and High Frequency Filters," TFR Technologies, Inc., (Jun. 1, 2001), pp. 1-18.
F. Engelmark, "AIN and High-k Thin Films for IC and Electroacoustic Applications," Comprehensive Summaries of Uppsala Dissertations from the Faculty of Science and Technology, vol. 757, ACTA Universitatis Upsaliensis, Uppsala, 2002.
K. Williams, et al., "Etch Rates for Micromachining Processing—Part II," Journal of Microelectromechanical Systems, vol. 12, No. 6, Dec. 2003, pp. 761-778.
D. Carter et al., "Fabrication and Measurement of an IC-Compatible GHZ-Range Piezoelectric Longitudinal Bar Resonator," Solid-State Sensor, Actuator and Microsystems Workshop, Hilton Head Island, South Carolina, Jun. 6-10, 2004, pp. 254-257.
J. H. Lee et al., "Effect of mass and stress on resonant frequency shift of functionalized Pb($Zr_{0.52}Ti_{0.48}$)$O_3$ thin film microcantilver for the detection of C-reactive protein," Applied Physics Letters, vol. 84, No. 16, Apr. 19, 2004, pp. 3187-3189.
G. Chapman et al, "Bi/In Thermal Resist for Both Si Anisotropic Wet Etching and Si/$SiO_2$ Plasma Etching," SPIE Micro04, Photonics West, Micromachining and Microfabrication Process Technology IX, vol. 5342, 2004.
V. Milanovic, "Multilevel Beam SOI-MEMS Fabrication and Applications," Journal of Microelectromechanical Systems, vol. 13, (Feb. 2004) pp. 19-30.

K. S. Ryu et al., "Precision Patterning of PDMS Thin Films: A New Fabrication Method and Its Applications," International Symposium on Micro Total Analysis System (uTAS), Nara, Japan, 2002.

Madou, M., "Fundamentals of Microfabrication," CRC Press, 1997.

B. J. Costello et al., "A Flexural-Plate-Wave Microbial Sensor," 1992 IEEE, pp. 69-72.

S. W. Wenzel, "A Multisensor Employing an Ultrasonic Lamb-Wave Oscillator," IEEE Transactions on Electron Devices, vol. 35, No. 6, Jun. 1988, pp. 735-743.

M. A. Dubois, "Thin Film Bulk Acoustic Wave Resonators: A Technology Overview," MEMSWAVE 03, Toulouse, France, Jul. 2-4, 2003.

Chen, Kuo-Shen et al., "Silicon Strength Testing for Mesoscale Structural Applications," Mat. Res. Soc. Symp. Proc. Vo. 518, (1998) pp. 123-130.

Chen, Kuo-Shen et al., "Controlling and Testing the Fracture Strength of Silicon on the Mesoscale," Journal of the American Ceramic Society, 83 [6] (2000), pp. 1476-1484.

Chen, Kuo-Shen et al., "Effect of Process Parameters on the Surface Morphology and Mechanical Performance of Silicon Structures After Deep Reactive Ion Etching (DRIE)," Journal of Microelectromechanical Systems, vol. 11, No. 3, Jun. 2002, pp. 264-275.

Hu, S. M., "Critical Stress in Silicon Brittle Fracture, and Effect of Ion Implantation and Other Surface Treatments," Journal of Applied Physics 53(5), May 1982, pp. 3576-3580.

Lin, Chung-Hsien et al., "Design and Fabrication of a Miniaturized Bulk Acoustic Filter by High Aspect Ratio Etching," J. Microlith., Microfab., Microsyst. (Jul.-Sep. 2005), vol. 4(3), pp. 033010-1-033010-7.

Wilson, Carol J., et al., "Fracture Testing of Bulk Silicon Microcantilever Beams Subjected to a Side Load," Journal of Microelectromechanical Systems, vol. 5, No. 3, Sep. 1996, pp. 142-150.

Yallup, Kevin, "The Application and Commercialization of SOI as a Material for Advanced Microsystems," Future Fab International, Issue 19, pp. 1-9, Available at (http://www.future-fab.com/documents.asp?grID=208&d_ID=1182, Last visited Sep. 6, 2005.

* cited by examiner

MICROFABRICATED DEVICES AND METHOD FOR FABRICATING MICROFABRICATED DEVICES

RELATED APPLICATIONS

This application claims priority to U.S. provisional application Ser. No. 60/793,848 filed on Apr. 21, 2006, and entitled "Methods for Fabricating Acoustic Devices," the entirety of which is incorporated herein by reference.

FIELD OF THE INVENTION

The present invention relates to microfabricated devices for operation in a fluid.

BACKGROUND OF THE INVENTION

Microfabricated devices can be used for a variety of fluid applications, including as sensors, valves, pumps and mixers. Microfabricated devices that are intended to operate in fluids must be designed and fabricated to ensure there is adequate fluid sealing of the device, fluid communication between the fluid and the sensing and/or actuation surface of the device, and isolation of the electrical interfaces from the fluid.

Microfabricated devices are often used to conduct chemical sensing or biological assays. For example, a microfabricated sensor can be used to detect the presence or quantify the amount of a biological analyte in a fluid sample. One approach is to immobilize antibodies specific to the analyte of interest on the sensor surface. Typically, an underlying surface chemistry layer is used to facilitate binding of biological molecules (e.g., antibodies) to a surface of the sensor. Analyte in a fluid sample binds to the immobilized antibodies on the sensor producing a change in the sensor response.

Microfabricated devices also can be used to characterize fluid properties. For example, microfabricated devices are sometimes used to measured density, viscosity and speed of sound in a fluid. Further, by monitoring the response of a sensor to changes in the fluid environment, various chemical or biochemical processes (e.g., reaction rate, phase change, aggregation) can be characterized. Some applications include, but are not limited to, monitoring polymerization processes or measuring material melt curves.

Some sensing applications are performed in conductive fluids (e.g., fluids that contain dissolved salts). Contact between a conductive fluid and electrical traces on the surface of the microfabricated device can result in electrical dissipation into the fluid or changes to the electrical impedance between adjacent electrical traces. Dissipation into a conductive fluid results in a loss of performance and potentially, heating of the microfabricated device and the fluid. A change in the electrical impedance between adjacent electrical traces also interferes with the proper functioning of the microfabricated device in cases where it is necessary to have high impedance isolation between adjacent electrical traces. Further, microfabricated devices are sometimes used in fluids that are corrosive or are capable of adversely affecting the operation of the microfabricated device.

Some microfabricated devices (e.g., traditional flexural plate wave microfabricated devices) have a suspended membrane that is produced by performing a through-wafer etch. The electrical interface to the microfabricated devices resides on the side of the wafer opposite to the etched cavity. In operation, a fluid contacts the sensing surface of the microfabricated device through the cavity formed in the wafer. While this allows the fluid and electrical interfaces to be separated (located on opposite sides of the microfabricated device), it complicates the design of a fluid system using the microfabricated device and can result in poor performance. As the lateral dimensions of the device are reduced, injecting the fluid into the cavity becomes more challenging.

For example, some assays require uniform flow properties at the sensing surface (e.g., a membrane) of the microfabricated device. Injecting fluid into an etched cavity that defines the sensing surface results in a non-uniform fluid flow pattern at the sensing surface. In these cases, it may be advantageous to design a system that provides a substantially planar surface over which the fluid is directed.

In addition, chemically treating the sensing surface of the microfabricated device is challenging because the chemical treatment (e.g., a fluid) must be able to completely wet the cavity. Proper wetting of the cavity is difficult because the cavity has sharp corners (e.g., produced by, for example, a deep reactive ion etching process) which makes it difficult to insure that the entire cavity is adequately treated. Additionally, subsequent use of the device in operation is also challenging because the fluid introduced into the cavity of the microfabricated device also requires proper wetting of the cavity.

A need therefore exists for improved designs for microfabricated devices and improved methods for fabricated microfabricated devices.

SUMMARY OF THE INVENTION

The invention, in one aspect, features a microfabricated device for operation in a fluid. The device includes a substrate having a first and second surface. The device also includes a first electrode material layer located over the first surface of the substrate. The device also includes a piezoelectric material layer located over the first electrode material layer. The device also includes a second electrode material layer located over the piezoelectric material layer. The device also includes a layer of isolation material (e.g., low temperature oxide, nitride, polymer) located over the second electrode material layer that at least one of chemically or electrically isolates a portion of the second electrode material layer from a fluid.

In some embodiments, the device includes a layer of conductive material (e.g., a metal such as gold, silver or aluminum or a semiconductor material such as silicon) located over the layer of isolation material. The electrical potential of the layer of conductive material can be controlled to reduce the electrical interaction between the device and the fluid or a substance in the fluid. In some embodiments, the device includes a layer of immobilization material (e.g., metal, polymer, semiconductor or dielectric) located over the layer of isolation material to facilitate immobilization of a substance on the microfabricated device.

In some embodiments, the substrate includes a silicon layer having a first and second surface, a first silicon oxide layer adjacent the first surface of the silicon layer, a second silicon oxide layer adjacent the second surface of the silicon layer, a first silicon nitride layer adjacent the first silicon oxide layer having a surface that is the first surface of the substrate, and a second silicon nitride layer adjacent the second silicon oxide layer.

In some embodiments, the second electrode material layer is a layer of metal (e.g., molybdenum or layers of titanium and gold). In some embodiments, the device includes a cavity formed in the second silicon nitride layer, the second silicon oxide layer and the silicon layer exposing the first silicon nitride layer. In some embodiments, a portion of the silicon oxide layer between the silicon layer and the first silicon nitride layer is removed to form an undercut. In some embodiments, the isolation material is an oxide material (e.g., a low temperature oxide material).

In some embodiments, the first and/or second electrode material layer includes one or more electrodes. The one or more electrodes can be at least one sensing electrode and at least one actuation electrode. In some embodiments, the one or more electrodes can be a pair of sensing electrodes and a pair of actuation electrodes. In some embodiments, the first and/or second electrode material layers include an interdigitated sensing electrode pair and an interdigitated actuation electrode pair. In some embodiments, the microfabricated device is configured to operate as a flexural plate wave device.

In some embodiments, the device includes a layer of conductive material located over the layer of isolation material to facilitate immobilization of a substance on the microfabricated device. In some embodiments, the electrical potential of the layer of conductive material is controlled to reduce the electrical interaction between the microfabricated device and the fluid or a substance in the fluid. The substance can be, for example, whole cells, bacteria, yeast, fungi, blood cells, dissociated tissue cells, spores, viruses, proteins, antibodies, lipids, carbohydrates, nucleic acids, peptides or small molecules.

In some embodiments, the layer of conductive material is a barrier between the layer of isolation material and the fluid. In some embodiments, the device includes a fluid channel over the layer of isolation material to deliver the fluid to a surface of the layer of isolation material. In some embodiments, a signal output by the first and second electrode material layers is representative of the propagation characteristics of a structure that incorporates the piezoelectric material layer.

The invention, in another aspect, features a microfabricated device for operation in a fluid that includes a substrate having a first insulating surface and a second surface. The device also includes a first electrode material layer located over the first surface of the substrate, the first electrode material layer having one or more electrodes. The device also includes a piezoelectric material layer located over the first electrode material layer. The device also includes a second electrode material layer located over the piezoelectric material layer, the second electrode material layer functioning as an electrical ground plane and defining a fluid interface for the microfabricated device.

In some embodiments, the device includes a layer of isolation material located over the second electrode material layer that at least one of chemically or electrically isolates a portion of the second electrode material layer from the fluid. In some embodiments, the device includes a layer of conductive material located over the layer of isolation material. The electrical potential of the layer of conductive material can be controlled to reduce the electrical interaction between the microfabricated device and the conductive fluid or a substance in the conductive fluid. In some embodiments, the device includes a layer of immobilization material located over the layer of isolation material to facilitate immobilization of a substance on the microfabricated device.

In some embodiments, the substrate includes a silicon layer having a first and second surface, a first silicon oxide layer adjacent the first surface of the silicon layer, a second silicon oxide layer adjacent the second surface of the silicon layer, a first silicon nitride layer adjacent the first silicon oxide layer having a surface that is the first surface of the substrate, a second silicon nitride layer adjacent the second silicon oxide layer. In some embodiments, the substrate includes a silicon layer having a first and second surface, a first silicon oxide layer adjacent the first surface of the silicon layer, a second silicon oxide layer adjacent the second surface of the silicon layer, a first silicon nitride layer adjacent the first silicon oxide layer, and a second silicon nitride layer adjacent the second silicon oxide layer and having a surface that is the first surface of the substrate. In some embodiments, the second electrode material layer is a layer of metal, a conductive semiconductor or other conductive material.

The invention, in another aspect, relates to a method for fabricating a microfabricated device for operation in a fluid. The method involves depositing a piezoelectric material layer over a first surface of a substrate. The method also involves creating an electrode material layer over the piezoelectric material layer. The method also involves creating an isolation material layer over the electrode material layer that at least one of chemically or electrically isolates a portion of the electrode material layer from a fluid during operation of the microfabricated device.

In some embodiments, an electrode material layer is provided over the first surface of the substrate prior to depositing the piezoelectric material layer over the first surface of the substrate. In some embodiments, the first surface of the substrate comprises a layer of silicon material. In some embodiments, the method includes creating a layer of conductive material located over the layer of isolation material. The electrical potential of the layer of conductive material can be controlled to reduce the electrical interaction between the microfabricated device and the fluid or a substance in the fluid.

In some embodiments, the method involves etching a cavity in the second surface of the substrate. In some embodiments, the method involves etching an oxide material layer of the substrate, exposed by the etching of the cavity in the second surface of the substrate, to create an undercut in the oxide material layer. Creating the isolation material layer over the electrode material layer can involve depositing an isolation material. Creating an electrode material layer over the piezoelectric material layer can involve depositing an electrode material over the piezoelectric material layer and forming one or more electrode structures.

In some embodiments, the method involves etching the isolation layer material, electrode material layer and piezoelectric material layer to form at least one via exposing a portion of the substrate to provide electrical connection to an electrical ground layer in the substrate. In some embodiments, the method involves etching the isolation layer material to form at least one via exposing a portion of the electrode material layer to provide electrical connection to the electrode material layer. In some embodiments, the substrate includes a silicon layer having a first and second surface, a first silicon oxide layer adjacent the first surface of the silicon layer, a second silicon oxide layer adjacent the second surface of the silicon layer, a first silicon nitride layer adjacent the first silicon oxide layer having a surface that is the first surface of the substrate, a second silicon nitride layer adjacent the second silicon oxide layer.

The invention, in another aspect, relates to a method for fabricating a microfabricated device for operation in a fluid. The method involves creating a first electrode material layer over a first surface of a substrate, the first electrode material layer having one or more electrodes. The method also involves depositing a piezoelectric material layer over the first electrode material layer. The method also involves creating a second electrode material layer located over the piezoelectric material layer, the second electrode material layer functioning as an electrical ground plane and defining a fluid interface for the microfabricated device.

In some embodiments, the method involves creating a layer of isolation material located over the second electrode material layer that at least one of chemically or electrically isolates a portion of the second electrode material layer from the fluid. In some embodiments, the method involves creating a layer of conductive material located over the layer of isolation material. The electrical potential of the layer of conductive material can be controlled to reduce the electrical interaction between the microfabricated device and the fluid or a substance in the fluid.

In some embodiments, the method involves creating a layer of immobilization material located over the layer of isolation material to facilitate immobilization of a substance on the microfabricated device. In some embodiments, the first electrode material layer is a layer of silicon.

The invention, in another aspect, features a microfabricated device for operation in a fluid. The device includes a substrate having a first and second surface. The device also includes a first electrode material layer located over the first surface of the substrate. The device also includes a piezoelectric material layer located over the first electrode material layer. The device also includes a second electrode material layer located over the piezoelectric material layer. The device also includes a means for at least one of chemically or electrically isolating the second electrode material layer from a fluid.

The foregoing and other objects, aspects, features, and advantages of the invention will become more apparent from the following description and from the claims.

BRIEF DESCRIPTION OF THE DRAWINGS

The foregoing and other objects, feature and advantages of the invention, as well as the invention itself, will be more fully understood from the following illustrative description, when read together with the accompanying drawings which are not necessarily to scale.

DETAILED DESCRIPTION OF ILLUSTRATIVE EMBODIMENTS

Figure 1:
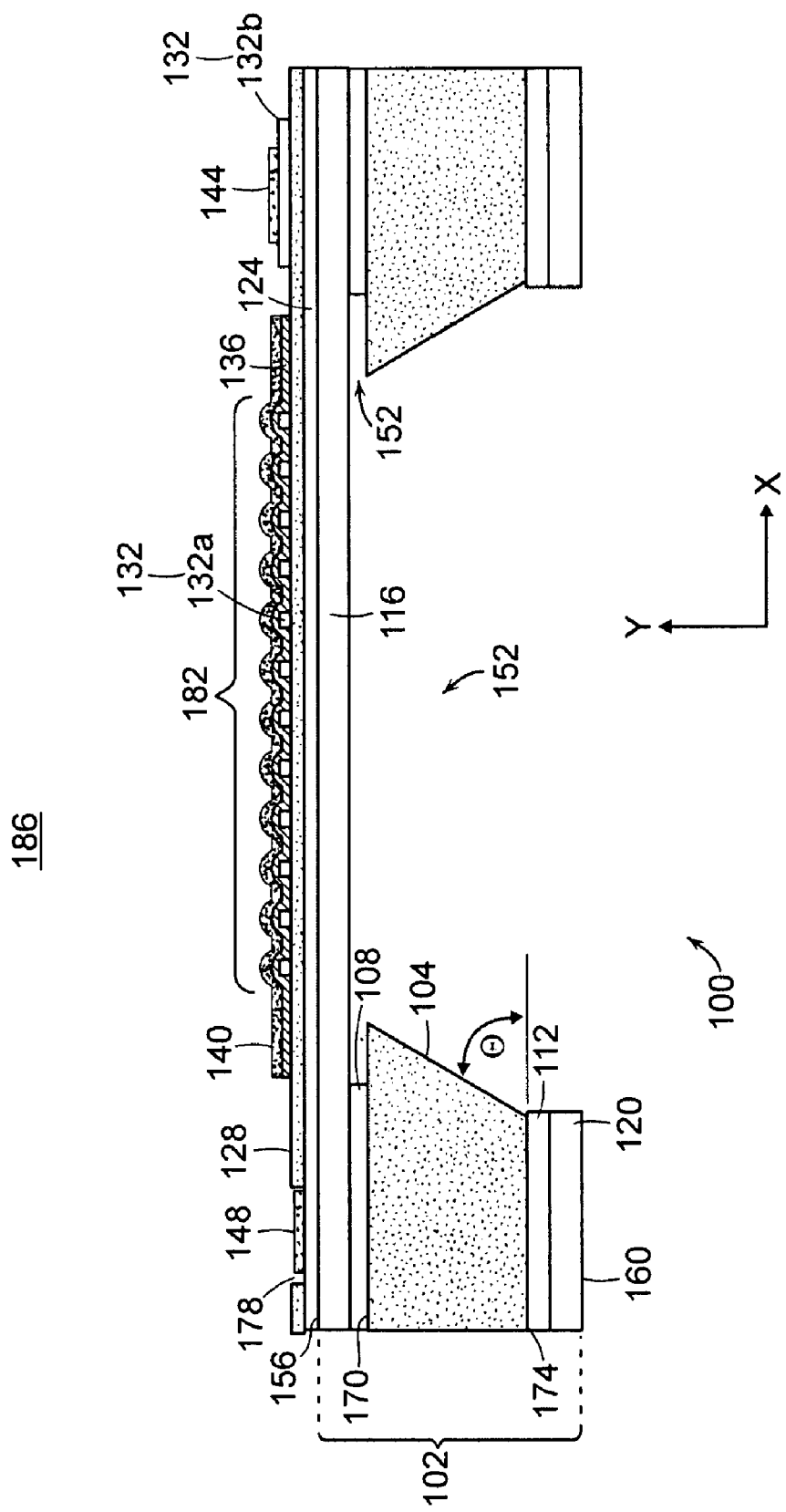
FIG. 1 is a schematic illustration of a microfabricated device, according to an illustrative embodiment of the invention.

FIG. 1 is a schematic illustration of a microfabricated device 100, according to an illustrative embodiment of the invention. The device 100 includes a substrate 102 having a first surface 156 and a second surface 160. The substrate 102 includes a handle wafer 104 (e.g., a silicon wafer that is conductive, preferably with a resistivity of about 1-10 ohm-cm) having a first surface 170 and a second surface 174. The substrate 102 also includes a first oxide material layer 108 and a second oxide material layer 112 The first oxide material layer 108 is located over the first surface 170 of the handle wafer 104. The second oxide material layer 112 is located over the second surface 174 of the handle wafer 104. In some embodiments, the oxide material layers are layers of silicon oxide that are thermally grown on the surfaces of the handle wafer 104.

The substrate 102 also includes a first silicon nitride layer 116 located over the first oxide material layer 108. The substrate 102 also includes a second silicon nitride layer 120 located over the second oxide material layer 112. In some embodiments, the silicon nitride layers are deposited using a low pressure chemical vapor deposition (LPCVD) process. In this embodiment, the first surface 156 of the substrate 102 is also the first surface of the first silicon nitride layer 116. By varying the ratio of silicon to nitrogen in the coating, the stress in the material can be controlled. For devices that include a suspended membrane structure, it is desirable to tailor the stress of the coating to be moderately tensile (e.g., low-stress LPCVD silicon nitride coating with 50-200 MPa of tensile stress).

The device 100 also includes a first electrode material layer 124 located over (also referred to herein generally as located adjacent) the first surface 156 of the substrate 102. In some embodiments, the first electrode material layer 124 (as well as other electrode material layers) is molybdenum that is sputtered on to the first surface 156 of the substrate 102. Molybdenum is used as an electrode material layer because it is a high temperature metal with good adhesion properties. The high temperature capability of molybdenum allows subsequent material layers (e.g., aluminum nitride piezoelectric layer and silicon oxide layers) to be deposited. The process temperature for depositing piezoelectric materials and silicon oxide materials generally exceeds 300 C., and molybdenum does not degrade under these conditions. Additionally, molybdenum has good adhesion properties when used in combination with many piezoelectric materials and oxide materials. Other metals and other conductive materials common in integrated circuit design can, however, also be used as an electrode material layer.

In some embodiments, an intermediate layer is first applied to the first surface 156 of the substrate 102, prior to application of the first electrode material layer 124. In one embodiment, the intermediate layer improves the subsequent bonding of the first electrode material layer 124 to the substrate 102. Generally, intermediate material layers are sometimes used during fabrication to, for example, improve the bonding between two materials or electrically or chemically isolate one material layer from another.

The device 100 also includes a piezoelectric material layer 128 located over the first electrode material layer 124. In some embodiments, the piezoelectric material layer 128 is, for example, aluminum nitride that is applied to the substrate by, for example, reactive sputtering of the aluminum nitride. Other suitable microfabrication techniques may, alternatively, be used to apply the piezoelectric material layer 128 over the first electrode material layer 124. The device 100 also includes a second electrode material layer 132 located over the piezoelectric material layer 128. In this embodiment, the second electrode material layer 132 includes a plurality of electrodes 132*a*. The second electrode material layer 132 also includes an electrode contact pad 132*b* that is in electrical communication with the electrodes 132a. The electrode contact pad 132b is located adjacent to the electrodes 132a such that subsequent material layers (e.g., isolation material layer 140) applied over the electrodes 132a do not cover the electrode contact pad 132b. In this manner, the electrode contact pad 132b provides electrical connection to the electrodes 132a.

A via 178 is located in the piezoelectric material layer 128 providing access to the first electrode material layer 124. The via 178 can be created using one of many suitable semiconductor fabrication processes. For example, a photoresist material can be applied over the device 100 such that the surface of the device 100 is protected from an etchant other than in the desired location of the via 178. An optional electrical contact metallization layer 144 can be applied to the electrode contact pad 132b to facilitate attachment of an electrical connection to the device 100. In addition, an optional electrical contact metallization layer 148 can be applied to the first electrode material surface 124 to facilitate attachment of another electrical connection to the device 100.

The device 100 also defines a cavity 152 in the substrate 102 produced by, for example, an etching process. In this embodiment, the cavity 152 was produced using an etching process that is constrained by the crystal lattice structure of the handle wafer 104. By way of example, an anisotropic etchant used to etch a silicon wafer produces a cavity in which walls of the handle wafer 104 are at an angle Θ that is aligned with the crystal lattice structure of the handle wafer 104. In contrast, an isotropic etchant is not constrained by the crystal lattice structure of the handle wafer. The portion of the oxide layer 108 that is exposed when creating the cavity 152 is removed using an etching process. Typically an isotropic etch is used to remove the exposed portion of the oxide layer material layer 108.

In an alternative embodiment, an anisotropic dry etch is instead used to etch the silicon wafer to produce a cavity in which walls of the handle wafer 104 are aligned along the Y-axis, perpendicular to the X-axis. For example, a deep reactive ion etching process is commonly used to achieve geometries such as these.

The substrate 102 also has a region in which an undercut 116 exists between the first silicon nitride layer 116 and the handle wafer 104. In this embodiment, the undercut 116 was produced using an etching process that etched a portion of the first oxide material layer 108 located between the first silicon nitride layer 116 and the handle wafer 104. In practice, the undercut 116 has been shown to improve the boundary conditions of the membrane 182 where the membrane 182 contacts the cavity 152 and, thus, improves the performance of the device 100.

The cavity 152 of the device 100 exposes the first silicon nitride layer 116 thereby defining a suspended membrane 182. The electrode material layers 132 and 124 are configured to allow a user or computer to monitor the vibrational characteristics of the membrane 182. In one embodiment, instrument/control electronics (not shown) apply a time-varying electrical signal to at least one electrode in the electrode material layers (via the electrical contact metallization layers) to generate vibrations in the membrane 182. The instrument/control electronics also monitor the vibrational characteristics of the membrane 182 by receiving a sensor signal from at least a second electrode in the electrode material layers. In some embodiments, the signals output by the first and second electrode material layers 124 and 132 are representative of the propagation characteristics (e.g., acoustic propagation characteristics) of the device 100 interacting with the fluid environment (or, for example, a structure that incorporates the piezoelectric material layer that interacts with the fluid environment). In some embodiments, the signals output by the first and second electrode material layers 124 and 132 are representative of the propagation characteristics (e.g., acoustic propagation characteristics) of the device interacting with substances in the fluid or substances attached to a surface of the device. The instrument/control electronics compare a reference signal to the signal from the second set of electrodes to determine the changes in the relative magnitude and phase angle of the signal as a function of frequency. The instrument/control electronics interpret these changes to detect the presence of a particular material in contact with a surface of the membrane 182.

In some embodiments, the membrane 182 is constructed such that the device 100 is a flexural plate wave (FPW) device in which the second electrode material layer 132a is configured such that there are two sets of interdigitated electrodes (one for actuation and one for sensing). Strain energy is carried in bending and tension in the FPW device. In some embodiments, it is desirable for the thickness-to-wavelength ratio of the FPW device to be less than one, and in some cases much less than one. In general, the wavelength "$\lambda$" of the FPW device is approximately equal to the pitch of the interdigitated electrodes. In one embodiment, the thickness-to-wavelength ratio of the FPW device is about 2 µm/38 µm. In other embodiments, the FPW device is designed to isolate a particular mode (e.g., any mode from the zero$^{th}$ order mode to higher order modes) or bandwidth of modes associated with the device. For example, an FPW device having a thickness/wavelength of 2 µm/38 µm would isolate the 80$^{th}$ mode of the FPW device. The FPW device can be designed to achieve this effect by selecting a particular pattern for the interdigitated electrodes deposited on the device. In this embodiment, the FPW device is rectangular in shape. The FPW device can, alternatively, be circular or elliptical, or some other planar shape.

In this embodiment, the device 100 is used in a fluid environment. The device 100 is exposed to fluid located in region 186. In this embodiment of the invention, the device 100 includes a layer of isolation material 136 located over the second electrode material layer 132a. In this manner, at least a portion of the second electrode material layer 132a is isolated from the fluid located in region 186. In some embodiments, the isolation material layer 136 chemically isolates the second electrode material layer from the fluid in the region 186. In some embodiments, the isolation material layer 136 electrically isolates the second electrode material layer from the fluid in the region 186. In some embodiments, the isolation material layer 136 both chemically and electrically isolates the second electrode material layer from the fluid in the region 186.

In some embodiments, the isolation material layer 136 is, for example, silicon oxide that is applied to the device 100 by, for example, a low temperature chemical vapor deposition (CVD) process. Other isolation materials or dielectric layer materials common to integrated circuit design can be used. Other suitable microfabrication techniques may, alternatively, be used to apply the isolation material layer 136 over the second electrode material layer 132a. In some embodiments, a layer of immobilization material (e.g., gold or another suitable material) is located over the isolation material layer 136 to facilitate immobilization of a substance on the microfabricated device 100. Substances that may be immobilized on the device 100 include, for example, antibodies, whole cells, bacteria, yeast, fungi, blood cells, dissociated tissue cells, spores, viruses, proteins, lipids, carbohydrates, nucleic acids, peptides and small molecules. The device 100 can be used as a biosensor when, for example, a biological substance is immobilized on a sensing surface of the device 100. For example, antibodies immobilized on the device surface can be used to capture corresponding proteins located in a fluid.

The device 100 also includes a conductive material layer 140 (e.g., a metal such as gold, silver or aluminum or a semiconductor such as, silicon, titanium, gold or combinations thereof) located over the isolation material layer 136. In some embodiments, a layer of titanium material is first deposited on the surface of the isolation material layer 136 prior to depositing a metal layer such as gold. In this embodiment, the layer of titanium material is used to promote adhesion between the layer of gold and the device 100. In some embodiments, the electrical potential of the conductive material layer 140 is controlled via an electrical connection to the conductive material layer 140 (not shown) to minimize electrical interaction between the device 100 and the fluid located in region 186 (or substances in the fluid or substances immobilized on the surface of the device 100 or substances that bind to the device 100). In some embodiments, the conductive material layer is a fluid interface/barrier between the fluid in the region 186 and the isolation material layer 136.

In some embodiments, the conductive material layer 140 (e.g., gold) also is used because it can be used for applying surface chemistry to the device 100 for subsequent immobilization of biological molecules on the gold surface for use as a biosensor. In this manner, the conductive material layer functions as an immobilization material layer to facilitate immobilization of a substance (e.g., biological materials) on the microfabricated device 100. For example, thiol chemistries are often used as a means for immobilizing biological materials on a gold coated surface.

Figure 2:
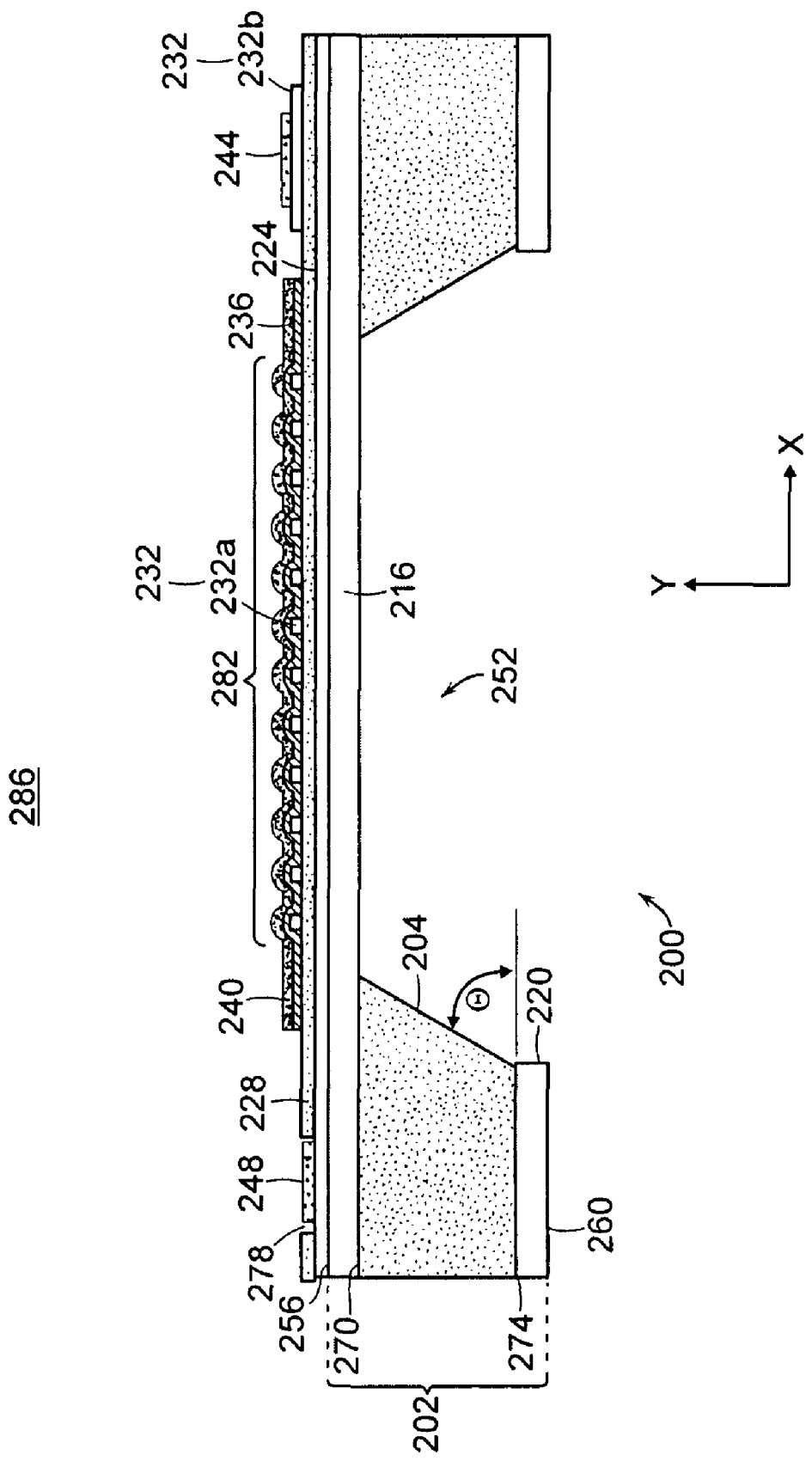
FIG. 2 is a schematic illustration of a microfabricated device, according to an illustrative embodiment of the invention.

FIG. 2 is a schematic illustration of a microfabricated device 200, according to an illustrative embodiment of the invention. The device 200 includes a substrate 202 having a first surface 256 and a second surface 260. The substrate 202 includes a handle wafer 204 (e.g., a silicon wafer that is conductive, preferably with a resistivity of about 1-10 ohm-cm) having a first surface 270 and a second surface 274.

The substrate 202 also includes a first silicon nitride layer 216 located over the first surface 270 of the handle wafer 204. The substrate 202 also includes a second silicon nitride layer 220 located over the second surface 274 of the handle wafer 204. In this embodiment, the first surface 256 of the substrate 202 is also the first surface of the first silicon nitride layer 216.

The device 200 also includes a first electrode material layer 224 located over (also referred to herein generally as located adjacent) the first surface 256 of the substrate 202. In some embodiments, an intermediate layer is first applied to the first surface 256 of the substrate 202, prior to application of the first electrode material layer 224 to improve the subsequent bonding of the first electrode material layer 224 to the substrate 202.

The device 200 also includes a piezoelectric material layer 228 located over the first electrode material layer 224. The device 100 also includes a second electrode material layer 232 located over the piezoelectric material layer 228. In this embodiment, the second electrode material layer 232 includes a plurality of electrodes 232a. The second electrode material layer 232 also includes an electrode contact pad 232b that is in electrical communication with the electrodes 232a. The electrode contact pad 232b is located adjacent to the electrodes 232a such that subsequent material layers (e.g., isolation material layer 240) applied over the electrodes 232a do not cover the electrode contact pad 232b. In this manner, the electrode contact pad 232b provides electrical connection to the electrodes 232a.

A via 278 is located in the piezoelectric material layer 228 providing access to the first electrode material layer 224. An optional electrical contact metallization layer 244 is applied to the electrode contact pad 232b to facilitate attachment of an electrical connection to the device 200. In addition, an optional electrical contact metallization layer 248 is applied to the first electrode material surface 224 to facilitate attachment of another electrical connection to the device 200.

The device 200 also defines a cavity 252 in the substrate 202 produced by, for example, an etching process. In this embodiment, the cavity 252 was produced using an etching process that is constrained by the crystal lattice structure of the handle wafer 204. By way of example, an anisotropic etchant used to etch a silicon wafer produces a cavity in which walls of the handle wafer 204 are at an angle Θ that is aligned with the crystal lattice structure of the handle wafer 204. In contrast, an isotropic etchant are not constrained by the crystal lattice structure of the handle wafer. The cavity 252 of the device 200 exposes the first silicon nitride layer 216 thereby defining a suspended membrane 282, similarly as described previously herein.

In this embodiment, the device 200 is used in a fluid environment. The device 200 is exposed to fluid located in region 286. In this embodiment of the invention, the device 200 includes a layer of isolation material 236 located over the second electrode material layer 232a. In this manner, at least a portion of the second electrode material layer 232a is isolated from the fluid located in region 286. In some embodiments, the isolation material layer 236 chemically isolates the second electrode material layer from the fluid in the region 286. In some embodiments, the isolation material layer 236 electrically isolates the second electrode material layer from the fluid in the region 286. In some embodiments, the isolation material layer 236 both chemically and electrically isolates the second electrode material layer from the fluid in the region 286.

In some embodiments, the isolation material layer 236 is, for example, silicon oxide that is applied to the device 200 by, for example, a low temperature chemical vapor deposition (CVD) process. In some embodiments, a layer of immobilization material (e.g., gold or another suitable material) is located over the isolation material layer 236 to facilitate immobilization of a substance on the microfabricated device 200.

The device 200 also includes a conductive material layer 240 (e.g., a metal such as gold, silver or aluminum or semiconductor such as silicon, or combinations thereof) located over the isolation material layer 236. In some embodiments, a layer of titanium material is first deposited on the surface of the isolation material layer 236, prior to depositing a metal layer such as gold. In this embodiment, the layer of titanium material is used to promote adhesion between the layer of gold and the device 200. In some embodiments, the electrical potential of the conductive material layer 240 is controlled via an electrical connection to the conductive material layer 240 (not shown) to minimize electrical interaction between the device 200 and the fluid located in region 286 (or substances in the fluid). In some embodiments, the conductive material layer is a barrier between the fluid in the region 286 and the isolation material layer 236.

In some embodiments, the conductive material layer 240 (e.g., gold) also is used because it can be used for applying surface chemistry to the device 200 for subsequent immobilization of biological molecules on the gold surface for use as a biosensor. In this manner, the conductive material layer functions as immobilization material layer to facilitate immobilization of a substance (e.g., biological materials) on the microfabricated device 200. For example, thiol chemistries are often used as a means for immobilizing biological materials on a gold coated surface.

Figure 3:
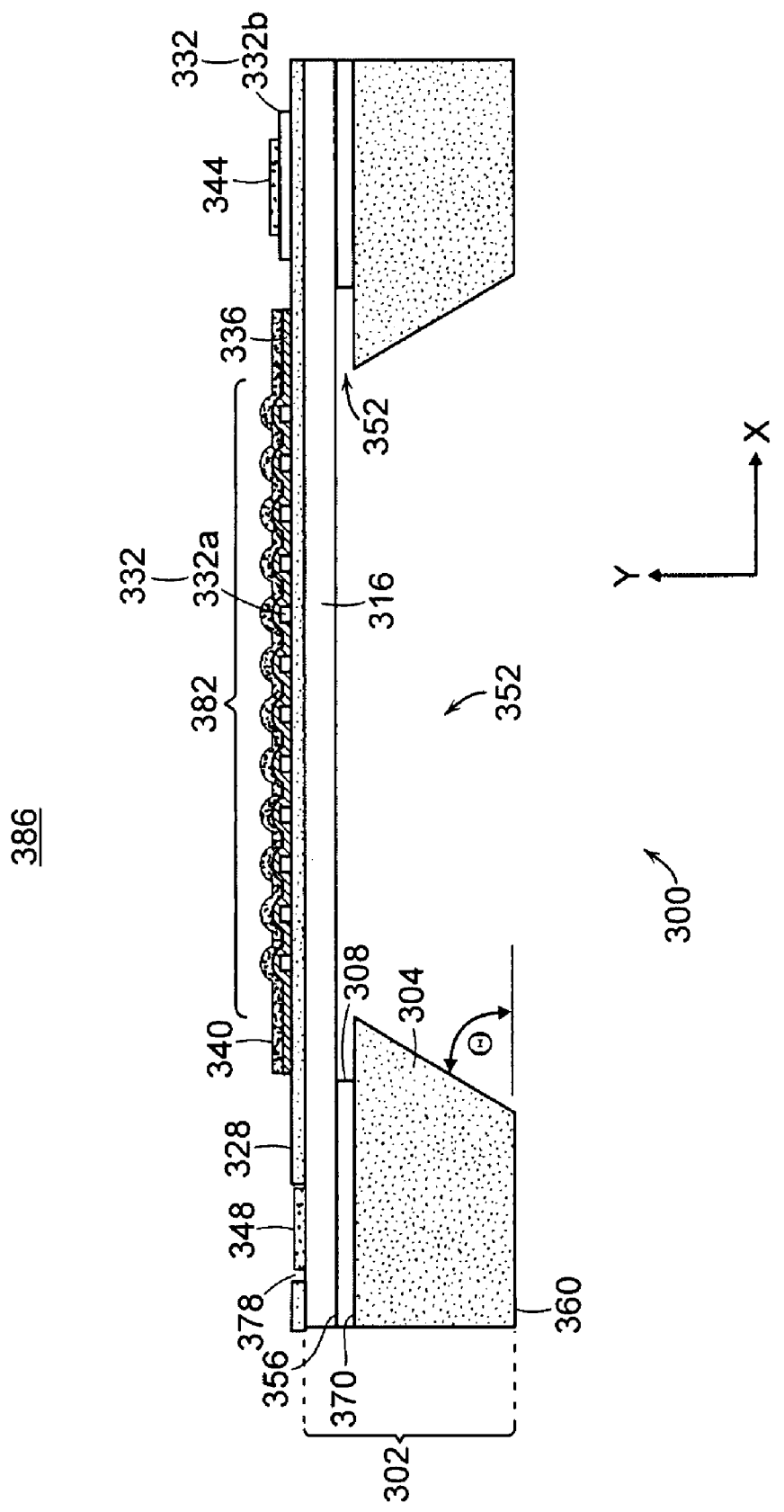
FIG. 3 is a schematic illustration of a microfabricated device, according to an illustrative embodiment of the invention.

FIG. 3 is a schematic illustration of a microfabricated device 300, according to an illustrative embodiment of the invention. The device 300 includes a substrate 302 having a first surface 356 and a second surface 360. The substrate 302 includes a handle wafer 304 (e.g., a silicon wafer that is conductive, preferably with a resistivity of about 1-10 ohm-cm) having a first surface 370 and a second surface that is the same as the second surface 360 of the substrate 302. The substrate 302 also includes a first oxide material layer 308 located over the first surface 370 of the handle wafer 304.

The substrate 302 also includes a layer of silicon material 316 located over the first oxide material layer 308. In this embodiment, the first surface 356 of the substrate 302 is also the first surface of the layer of silicon material 316. In this embodiment, the layer of silicon material 316 is sufficiently electrically conductive to function as an electrode material layer. In one embodiment, dopant is implanted into the layer of silicon material 316 so its electrical resistance is sufficiently small (for example, providing a sheet resistance of less than 50 ohm/square).

The device 300 also includes a piezoelectric material layer 328 located over the layer of silicon material 316. The device 300 also includes a second electrode material layer 332 located over the piezoelectric material layer 328. In this embodiment, the second electrode material layer 332 includes a plurality of electrodes 332a. The second electrode material layer 332 also includes an electrode contact pad 332b that is in electrical communication with the electrodes 332a. The electrode contact pad 332b is located adjacent to the electrodes 332a such that subsequent material layers (e.g., isolation material layer 340) applied over the electrodes 332a do not cover the electrode contact pad 332b. In this manner, the electrode contact pad 332b provides electrical connection to the electrodes 332a.

A via 378 is located in the piezoelectric material layer 328 providing access to the layer of silicon material 316 (which is conductive). An optional electrical contact metallization layer 344 is applied to the electrode contact pad 332b to facilitate attachment of an electrical connection to the device 300. In addition, an optional electrical contact metallization layer 348 is applied to the layer of silicon material 316 in the location of the via 378 to facilitate attachment of another electrical connection to the device 300.

The device 300 also defines a cavity 352 in the substrate 302 produced by, for example, an etching process. In this embodiment, the cavity 352 was produced using an etching process that is constrained by the crystal lattice structure of the handle wafer 304. By way of example, an anisotropic etchant used to etch a silicon wafer produces a cavity in which walls of the handle wafer 304 are at an angle Θ that is aligned with the crystal lattice structure of the handle wafer 304.

The cavity 352 of the device 300 exposes the layer of silicon material 316 thereby defining a suspended membrane 382, similarly as previously described herein. The substrate 302 also has a region in which an undercut 316 exists between the layer of silicon material 316 and the handle wafer 304. In this embodiment, the undercut 316 was produced using an etching process that etched a portion of the first oxide material layer 308 located between the layer of silicon material 316 and the handle wafer 304.

In this embodiment, the device 300 is used in a fluid environment. The device 300 is exposed to fluid located in region 386. In this embodiment of the invention, the device 300 includes a layer of isolation material 336 located over the second electrode material layer 332a. In this manner, at least a portion of the second electrode material layer 332a is isolated from the fluid located in region 386. In some embodiments, the isolation material layer 336 chemically isolates the second electrode material layer from the fluid in the region 386. In some embodiments, the isolation material layer 336 electrically isolates the second electrode material layer from the fluid in the region 386 (or substances in the fluid or substances immobilized on the surface of the device 300 or substances that bind to the device 300). In some embodiments, the isolation material layer 336 both chemically and electrically isolates the second electrode material layer from the fluid in the region 386.

The device 300 also includes a conductive material layer 340 (e.g., a metal such as gold, silver or aluminum or semiconductor such as silicon or combinations thereof) located over the isolation material layer 336. In some embodiments, a layer of titanium material is first deposited on the surface of the isolation material layer 336, and then a layer of metal (e.g., gold) is deposited over the layer of titanium material. In this embodiment, the layer of titanium material is used to promote adhesion between the layer of gold and the device 300. In some embodiments, the electrical potential of the conductive material layer 340 is controlled via an electrical connection to the conductive material layer 340 (not shown) to minimize electrical interaction between the device 300 and the fluid located in region 386 (or substances in the fluid). In some embodiments, the conductive material layer is a barrier between the fluid in the region 386 and the isolation material layer 336.

In some embodiments, the conductive material layer 340 (e.g., gold) also is used because it can be used for applying surface chemistry to the device 300 for subsequent immobilization of biological molecules on the gold surface for use as a biosensor. In this manner, the conductive material layer functions as immobilization material layer to facilitate immobilization of a substance (e.g., biological materials) on the microfabricated device 300. For example, thiol chemistries are often used as a means for immobilizing biological materials on a gold coated surface.

Figure 4:
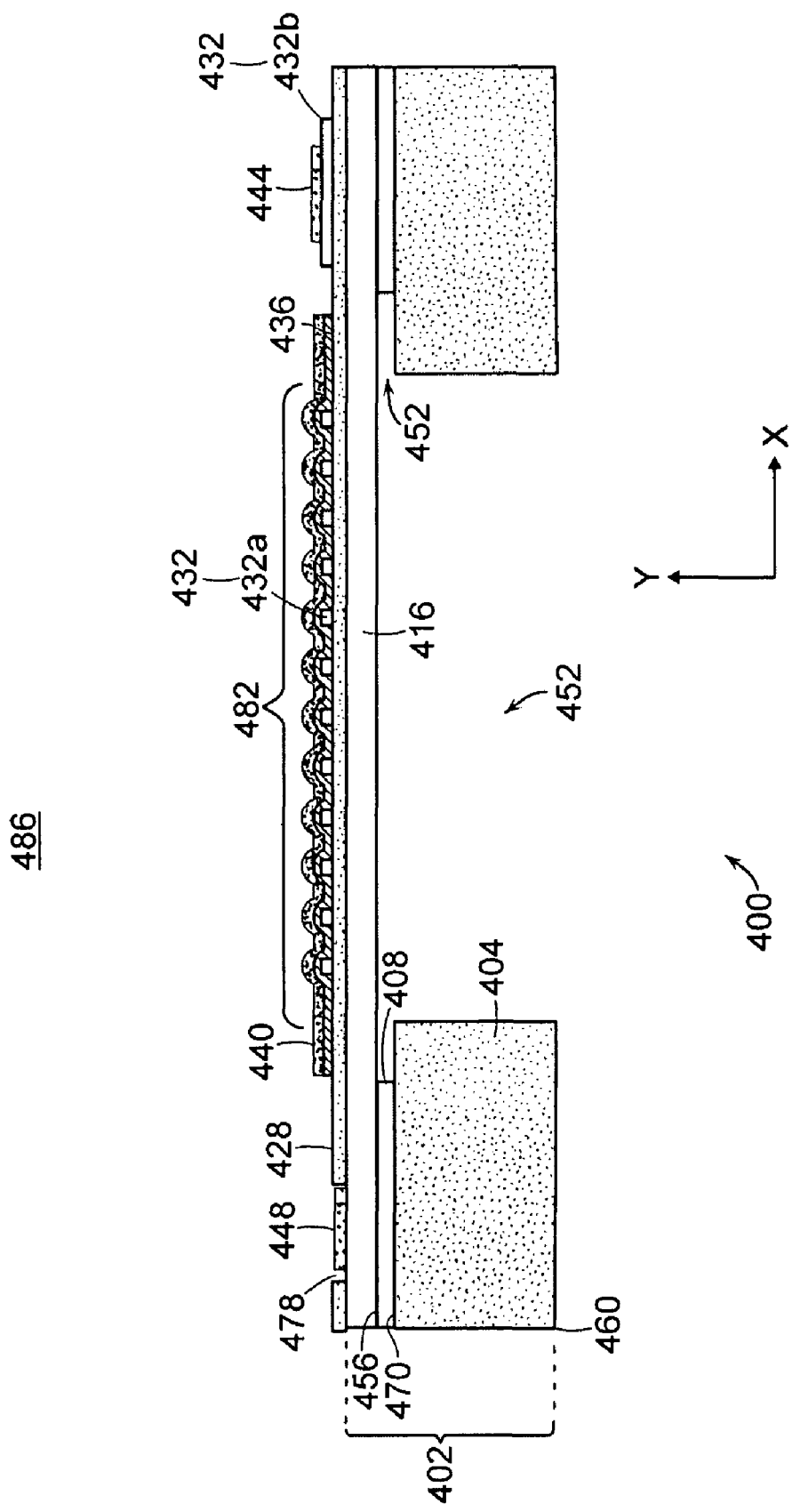
FIG. 4 is a schematic illustration of a microfabricated device, according to an illustrative embodiment of the invention.

FIG. 4 is a schematic illustration of a microfabricated device 400, according to an illustrative embodiment of the invention. The device 400 includes a substrate 402 having a first surface 456 and a second surface 460. The substrate 402 includes a handle wafer 404 (e.g., a silicon wafer that is conductive, preferably with a resistivity of about 1-10 ohm-cm) having a first surface 470 and a second surface that is the same as the second surface 460 of the substrate 402. The substrate 402 also includes a first oxide material layer 408 located over the first surface 470 of the handle wafer 404.

The substrate 402 also includes a layer of silicon material 416 located over the first oxide material layer 408. In this embodiment, the first surface 456 of the substrate 402 is also the first surface of the layer of silicon material 416. In this embodiment, the layer of silicon material 416 is sufficiently electrically conductive to function as an electrode material layer. In one embodiment, a dopant is implanted into the layer of silicon material 416 so its electrical resistance is sufficiently small (for example, providing a sheet resistance of less than 50 ohm/square).

The device 400 also includes a piezoelectric material layer 428 located over the layer of silicon material 416. The device 400 also includes a second electrode material layer 432 located over the piezoelectric material layer 428. In this embodiment, the second electrode material layer 432 includes a plurality of electrodes 432a. The second electrode material layer 432 also includes an electrode contact pad 432b that is in electrical communication with the electrodes 432a. The electrode contact pad 432b is located adjacent to the electrodes 432a such that subsequent material layers (e.g., isolation material layer 440) applied over the electrodes 432a do not cover the electrode contact pad 432b. In this manner, the electrode contact pad 432b provides electrical connection to the electrodes 432a.

A via 478 is located in the piezoelectric material layer 428 providing access to the layer of silicon material 416 (which is conductive). An optional electrical contact metallization layer 444 is applied to the electrode contact pad 432b to facilitate attachment of an electrical connection to the device 400. In addition, an optional electrical contact metallization layer 448 is applied to the layer of silicon material 416 in the location of the via 478 to facilitate attachment of another electrical connection to the device 400.

The device 400 also defines a cavity 452 in the substrate 402 produced by, for example, an etching process. In this embodiment, the cavity 452 was produced using an etching process that is not constrained by the crystal lattice structure of the handle wafer 404. By way of example, an anisotropic dry etch used to etch a silicon wafer produces a cavity in which walls of the handle wafer 404 are aligned along the Y-axis, perpendicular to the X-axis. For example, a deep reactive ion etching process is commonly used to achieve geometries such as these.

The cavity 452 of the device 400 exposes the layer of silicon material 416 thereby defining a suspended membrane 482, similarly as previously described herein. The substrate 402 also has a region in which an undercut 416 exists between the layer of silicon material 416 and the handle wafer 404. In this embodiment, the undercut 416 was produced using an etching process that etched a portion of the first oxide material layer 408 located between the layer of silicon material 416 and the handle wafer 404.

In this embodiment, the device 400 is used in a fluid environment. The device 400 is exposed to fluid located in region 486. In this embodiment of the invention, the device 400 includes a layer of isolation material 436 located over the second electrode material layer 432a. In this manner, at least a portion of the second electrode material layer 432a is isolated from the fluid located in region 486. In some embodiments, the isolation material layer 436 chemically isolates the second electrode material layer from the fluid in the region 486. In some embodiments, the isolation material layer 436 electrically isolates the second electrode material layer from the fluid in the region 486 (or substances in the fluid or substances immobilized on the surface of the device 400 or substances that bind to the device 400). In some embodiments, the isolation material layer 436 both chemically and electrically isolates the second electrode material layer from the fluid in the region 486.

The device 400 also includes a conductive material layer 440 (e.g., a metal such as gold, silver or aluminum or semiconductor such as silicon, or combinations thereof) located over the isolation material layer 436. In some embodiments, a layer of titanium material is first deposited on the surface of the isolation material layer 436 prior to depositing a metal layer such as gold. In this embodiment, the layer of titanium material is used to promote adhesion between the layer of gold and the device 400. In some embodiments, the electrical potential of the conductive material layer 440 is controlled via an electrical connection to the conductive material layer 440 (not shown) to minimize electrical interaction between the device 400 and the fluid located in region 486 (or substances in the fluid). In some embodiments, the conductive material layer is a barrier between the fluid in the region 486 and the isolation material layer 436.

In some embodiments, the conductive material layer 440 (e.g., gold) also is used because it can be used for applying surface chemistry to the device 400 for subsequent immobilization of biological molecules on the gold surface for use as a biosensor. In this manner, the conductive material layer functions as immobilization material layer to facilitate immobilization of a substance (e.g., biological materials) on the microfabricated device 400. For example, thiol chemistries are often used as a means for immobilizing biological materials on a gold coated surface.

Figure 5:
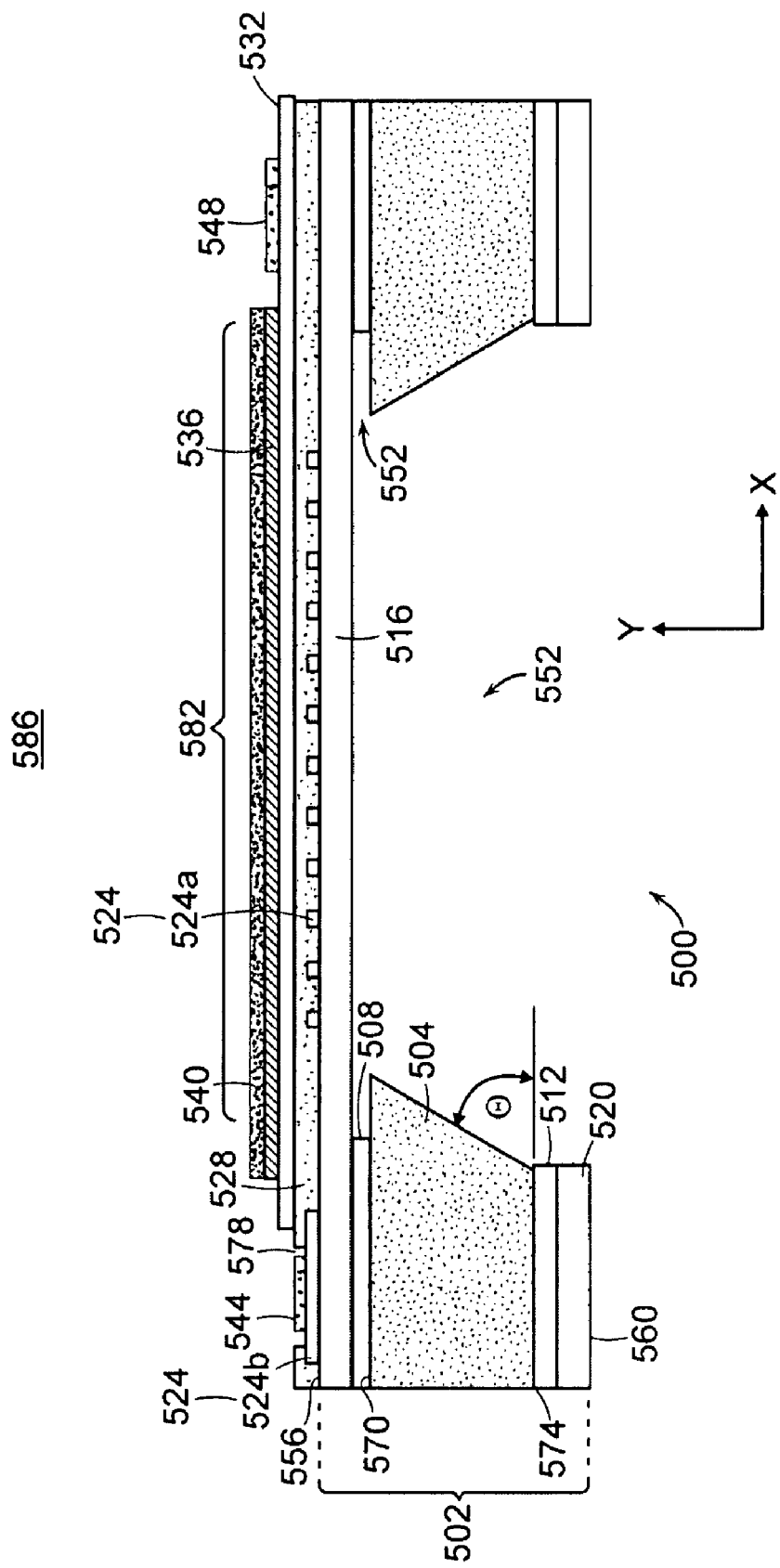
FIG. 5 a schematic illustration of a microfabricated device, according to an illustrative embodiment of the invention.

FIG. 5 is a schematic illustration of a microfabricated device 500, according to an illustrative embodiment of the invention. The device 500 includes a substrate 502 having a first surface 556 and a second surface 560. The substrate 502 includes a handle wafer 504 (e.g., a silicon wafer that is conductive, preferably with a resistivity of about 1-10 ohm-cm) having a first surface 570 and a second surface 574. The substrate 502 also includes a first oxide material layer 508 and a second oxide material layer 512 The first oxide material layer 508 is located over the first surface 570 of the handle wafer 504. The second oxide material layer 512 is located over the second surface 574 of the handle wafer 504.

The substrate 502 also includes a first silicon nitride layer 516 located over the first oxide material layer 508. The substrate 502 also includes a second silicon nitride layer 520 located over the second oxide material layer 512. In some embodiments, the silicon nitride layers are deposited using a low pressure chemical vapor deposition (LPCVD) process. By varying the ratio of silicon to nitrogen in the coating, the stress can be controlled. For devices that include a suspended membrane structure, it is desirable to tailor the stress of the coating to be moderately tensile (e.g., low-stress LPCVD silicon nitride coating with 50-200 MPa of tensile stress). In this embodiment, the first surface 556 of the substrate 502 is also the first surface of the first silicon nitride layer 516.

The device 500 also includes a first electrode material layer 524. In this embodiment, the first electrode material layer 524 includes a plurality of electrodes 524a. The second electrode material layer 524 also includes an electrode contact pad 524b that is in electrical communication with the electrodes 524a. The electrode contact pad 524b is located adjacent to the electrodes 524a such that subsequent material layers (e.g., isolation material layer 540) applied over the electrodes 524a do not cover the electrode contact pad 524b. In this manner, the electrode contact pad 524b provides electrical connection to the electrodes 524a.

The device 500 also includes a piezoelectric material layer 528 located over the first electrode material layer 524. In some embodiments, the piezoelectric material layer 528 is, for example, aluminum nitride that is applied to the substrate by, for example, reactive sputtering of the aluminum nitride. Other suitable microfabrication techniques may, alternatively, be used to apply the piezoelectric material layer 528 over the first electrode material layer 524.

The device 500 also includes a second electrode material layer 532 located over the piezoelectric material layer 528. A via 578 is located in the piezoelectric material layer 528 providing access to the electrode contact pad 524b. The via 578 can be created using one of many suitable semiconductor fabrication processes. An optional electrical contact metallization layer 548 is applied to the second electrode material surface 532 to facilitate attachment of an electrical connection to the device 500. In addition, an optional electrical contact metallization layer 544 is applied to the first electrode material surface 524b to facilitate attachment of another electrical connection to the device 500.

The device 500 also defines a cavity 552 in the substrate 502 produced by, for example, an etching process. In this embodiment, the cavity 552 was produced using an etching process that is constrained by the crystal lattice structure of the handle wafer 504. The etchant produces a cavity in which walls of the handle wafer 504 are at an angle Θ that is aligned with the crystal lattice structure of the handle wafer 504.

The cavity 552 of the device 500 exposes the first silicon nitride layer 516 thereby defining a suspended membrane 582, similarly as previously described herein. The substrate 502 also has a region in which an undercut 516 exists between the first silicon nitride layer 516 and the handle wafer 504.

In this embodiment, the device 500 is used in a fluid environment. The device 500 is exposed to fluid located in region 586. In this embodiment of the invention, the device 500 includes a layer of isolation material 536 located over the second electrode material layer 532. In this manner, at least a portion of the second electrode material layer 532 is isolated from the fluid located in region 586. In some embodiments, the isolation material layer 536 chemically isolates the second electrode material layer from the fluid in the region 586 (or substances in the fluid or substances immobilized on the surface of the device or substances that bind to the device).

In some embodiments, the isolation material layer 536 is, for example, silicon oxide that is applied to the device 500 by, for example, a low temperature chemical vapor deposition (CVD) process. Other isolation materials or dielectric layer materials common to integrated circuit design can be used. Other suitable microfabrication techniques may, alternatively, be used to apply the isolation material layer 536 over the second electrode material layer 532. In some embodiments, a layer of immobilization material (e.g., gold or another suitable material) is located over the isolation material layer 536 to facilitate immobilization of a substance on the microfabricated device 500. Substances that may be immobilized on the device 500 include, for example, whole cells, bacteria, yeast, fungi, blood cells, dissociated tissue cells, spores, viruses, proteins, antibodies, lipids, carbohydrates, nucleic acids, peptides and small molecules.

The device 500 also includes a conductive material layer 540 (e.g., a metal such as gold, silver or aluminum or semiconductor such as silicon, or combinations thereof) located over the isolation material layer 536. In some embodiments, a layer of titanium material is first deposited on the surface of the isolation material layer 532, and then a layer of metal (e.g., gold) is deposited over the layer of titanium material. In this embodiment, the layer of titanium material is used to promote adhesion between the layer of gold and the device 500. In some embodiments, the electrical potential of the conductive material layer 540 is controlled via an electrical connection to the conductive material layer 540 (not shown) to minimize electrical interaction between the device 500 and the fluid located in region 586 (or substances in the fluid or substances immobilized on the surface of the device 500 or substances that bind to the device 500). In some embodiments, the conductive material layer is a barrier between the fluid in the region 586 and the isolation material layer 536.

In some embodiments, the conductive material layer 540 (e.g., gold) also is used because it can be used for applying surface chemistry to the device 500 for subsequent immobilization of biological molecules on the gold surface for use as a biosensor. In this manner, the conductive material layer functions as immobilization material layer to facilitate immobilization of a substance (e.g., biological materials) on the microfabricated device 500.

Figure 6:
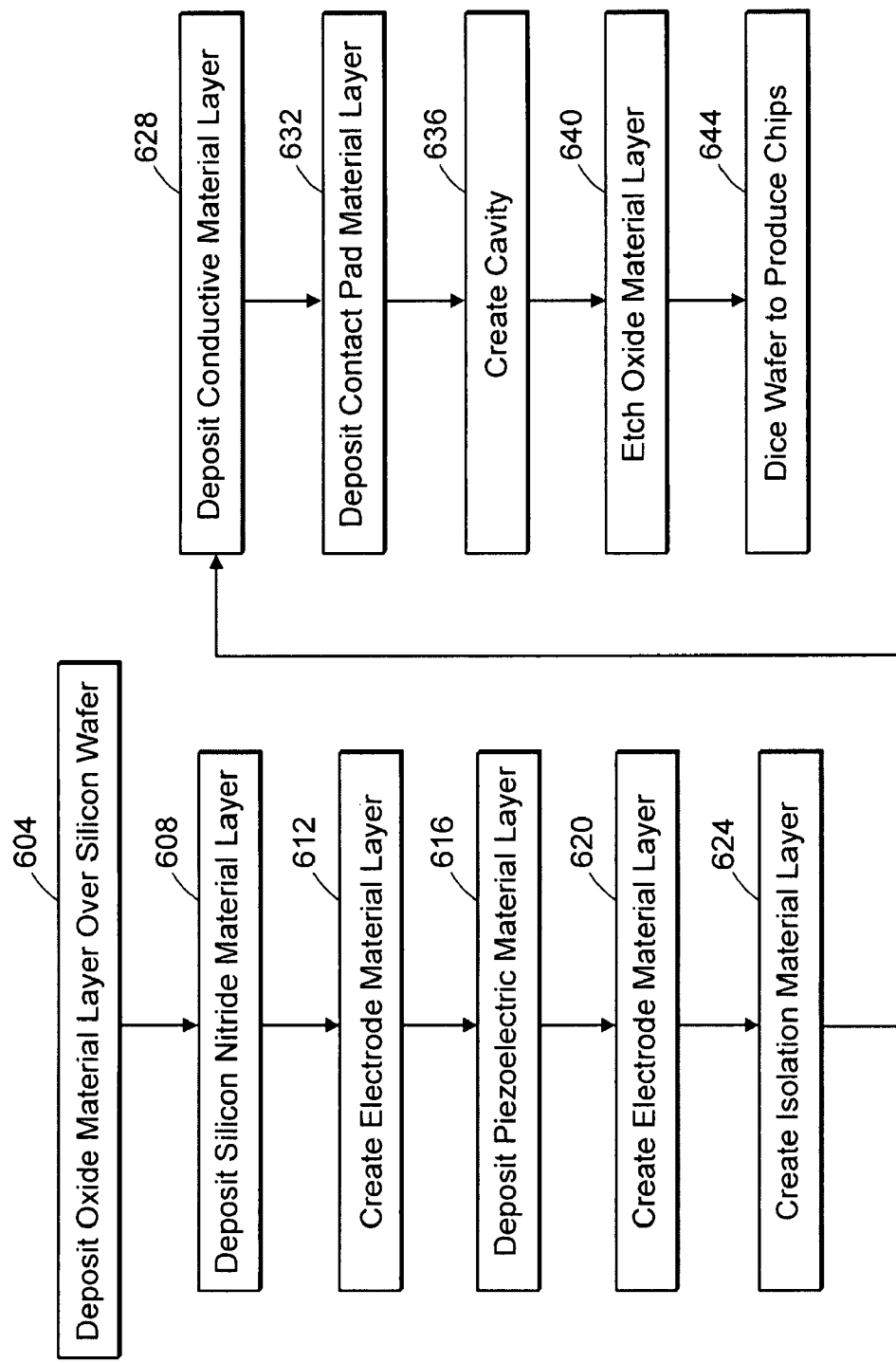
FIG. 6 is a flow diagram of a method for producing a microfabricated device, according to an illustrative embodiment of the invention.

FIG. 6 is a flow diagram of a method 600 for producing a microfabricated device (e.g., the microfabricated device 100 of FIG. 1), according to an illustrative embodiment of the invention. The method 600 involves depositing an oxide material layer (e.g., the first oxide material layer 108) over a silicon wafer (e.g., the handle wafer 104). In one embodiment, a one micron thick layer of thermal oxide is created or deposited (step 604) on a 500 micron thick silicon wafer (p-type boron-doped silicon with a resistivity of about 4-6 ohm-cm). In some embodiments, an oxide material layer (with a thickness between about 0.1 microns and about 10 microns) is deposited on a top and bottom surface (e.g., the first surface 156 and second surface 160) of the silicon wafer. In some embodiments, the handle wafer has a thickness between about 350 microns and about 1,000 microns).

The method 600 also involves depositing a silicon nitride material layer (step 608) over the oxide material layer. In one embodiment, a two micron thick layer of low stress silicon nitride is deposited over the oxide material layer using an LPCVD process. The deposition conditions are chosen to achieve a silicon nitride layer with moderate tensile stress (50-200 MPa). In some embodiments, the low stress silicon nitride layer has a thickness between about 0.1 microns and about 10 microns. In some embodiments, the oxide material layer is deposited over oxide material layers previously deposited on both the top and bottom surface of the silicon wafer.

The method 600 also involves creating a first electrode material layer (step 612) over the silicon nitride layer. In one embodiment, a 1500 angstrom thick layer of molybdenum is deposited over the silicon nitride layer using, for example a sputtering process. In some embodiments, the first electrode material layer substantially covers the silicon nitride layer and is used as a ground plane during operation of the microfabricated device. In some embodiments, the first electrode material layer has a thickness between about 500 angstroms and about 10,000 angstroms.

The method 600 also involves depositing a piezoelectric material layer (step 616) over the first electrode material layer. In one embodiment, a 5000 angstrom thick layer of aluminum nitride is deposited over the electrode material layer (e.g., the first electrode material layer 124) using a reactive sputtering process. In some embodiments, the piezoelectric material layer is between about 0.1 microns and about 3 microns.

The method 600 also involves creating a second electrode material layer (step 620) over the piezoelectric material layer (e.g., the second electrode material layer 132 over the piezoelectric material layer 128). In one embodiment, a 2000 angstrom thick layer of molybdenum is deposited over the piezoelectric material layer using a sputtering process. A photoresist material is applied to the second electrode material layer (applied in step 620) and then etched to produce a specific electrode pattern in the second electrode material layer. For example, in some embodiments, the second electrode material layer is covered with a photoresist and then etched to produce one or more electrodes (e.g., interdigitated electrodes) in the second electrode material layer. The one or more electrodes can be used as, for example, actuation and sensing electrodes. In some embodiments, however, a photoresist material is applied to the first electrode material layer (applied in step 612) and then etched to produce a specific electrode pattern in the first electrode material layer. In some embodiments, the second electrode material layer substantially covers the piezoelectric material layer and is used as a ground plane during operation of the microfabricated device. In some embodiments, the second electrode material layer has a thickness between about 500 angstroms and about 10,000 angstroms.

The method 600 also involves creating an isolation material layer (step 624) over the second electrode material layer. In one embodiment, a 1000 angstrom thick layer of low temperature silicon oxide is deposited over the second electrode material layer using a low temperature chemical vapor deposition process. In some embodiments, the isolation material layer has a thickness between about 500 angstroms and about 10,000 angstroms. The isolation material layer can then be processed to form one or more vias through the isolation material layer to provide access to underlying material layers. For example, a photoresist can be applied to the isolation material layer and then etched to form one or more vias through the isolation material layer and the piezoelectric material layer to expose the first electrode material layer and provide electrical access to the first electrode material layer. Further, a separate processing step can be performed in which a photoresist is applied to the isolation material layer and then etched to provide electrical access to the second electrode material layer.

The method 600 also involves depositing a conductive material layer (step 628) over the isolation material layer. In one embodiment, a 100 angstrom thick layer of titanium is deposited over the isolation material layer using, for example, an evaporation or sputtering process. Then, a 1000 angstrom thick layer of gold is deposited over the layer of titanium using, for example, an evaporation or sputtering process. In some embodiments, the conductive material layer has a thickness between about 500 angstroms and about 10,000 angstroms. The method 600 can also, optionally, involve depositing a contact metallization layer (e.g., electrical contact metallization layers 144 and 148) over exposed locations in the electrode material layers. The contact metallization layer material can be the same material or a different material than the material used for the conductive material layer.

The method 600 also involves forming or creating a cavity (step 636) through a portion of the microfabricated device. For example, with respect to FIG. 1, step 636 involves forming cavity 152 through the second silicon nitride layer 120, the second silicon oxide layer 112, the handle wafer 204 and the first silicon oxide layer 108 exposing the first silicon nitride layer 116, thereby forming the membrane 182. In one embodiment, the cavity is created by protecting the opposing side of the device and then using a potassium hydroxide (KOH) solution (e.g., a KOH bath) to create the cavity.

The method 600 also involves etching a portion of the first oxide material layer (step 640) to create an undercut between the first silicon nitride layer and the silicon wafer, similarly as described herein with respect to, for example, FIG. 1. In one embodiment, the undercut is formed using a buffered oxide etching (BOE) process or a diluted hydrofluoric (HF) acid etching process. The method 600 also involves dicing the wafer (step 644) produced by the previous steps to produce individual devices/chips.

Figure 7:
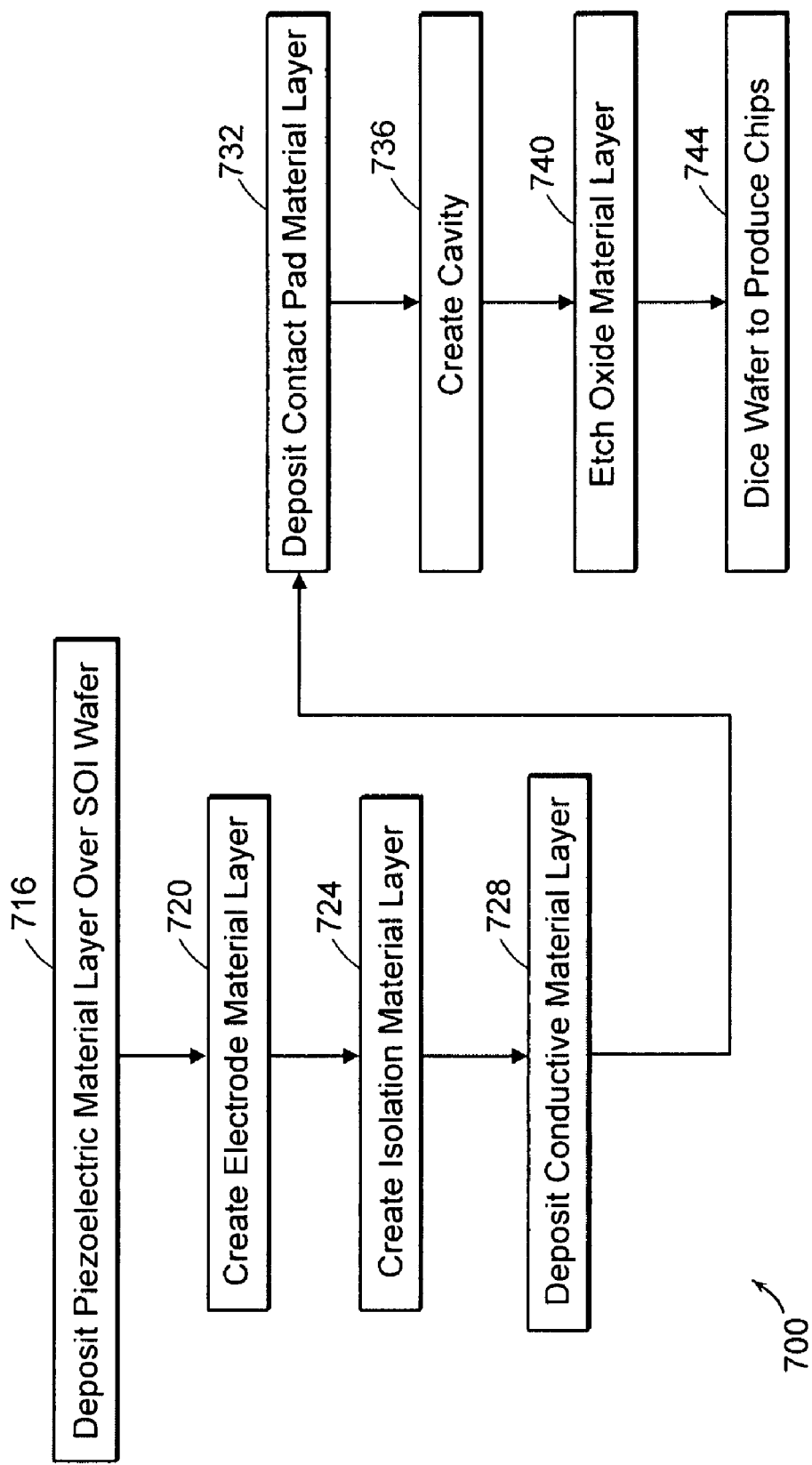
FIG. 7 is a flow diagram of a method for producing a microfabricated device, according to an illustrative embodiment of the invention.

FIG. 7 is a flow diagram of a method 700 for producing a microfabricated device (e.g., the microfabricated device 400 of FIG. 4), according to an illustrative embodiment of the invention. The method 700 involves depositing an oxide material layer (e.g., the first oxide material layer 408) over a silicon wafer (e.g., the handle wafer 404). The method 700 also involves depositing a silicon material layer over the oxide material layer. The combination of the silicon wafer (e.g., handle wafer 404), oxide material layer (e.g., oxide material layer 408) and silicon material layer (e.g., silicon material layer 416) produces a silicon on insulator (SOI) substrate (e.g., substrate 402). In this embodiment, the resistivity of the silicon material layer (e.g., silicon material layer 416) is adequate for the silicon material layer to function as an electrical ground plane for the device.

The method 700 also involves depositing a piezoelectric material layer (step 716) over the silicon material layer. The method 700 also involves creating a second electrode material layer (step 720) over the piezoelectric material layer (e.g., the second electrode material layer 432 over the piezoelectric material layer 428). A photoresist material is applied to the second electrode material layer (applied in step 720) and then etched to produce a specific electrode pattern in the second electrode material layer. For example, in some embodiments, the second electrode material layer is covered with a photoresist and then etched to produce one or more electrodes (e.g., interdigitated electrodes) in the second electrode material layer. The one or more electrodes can be used as, for example, actuation and sensing electrodes.

The method 700 also involves creating an isolation material layer (step 724) over the second electrode material layer. The isolation material layer can then be processed to form one or more vias through the isolation material layer to provide access to underlying material layers. For example, a photoresist can be applied to the isolation material layer and then etched to form one or more vias through the isolation material layer and the piezoelectric material layer to expose the first electrode material layer and provide electrical access to the first electrode material layer. Further, a separate processing step can be performed in which a photoresist is applied to the isolation material layer and then etched to provide electrical access to the second electrode material layer.

The method 700 also involves depositing a conductive material layer (step 728) over the isolation material layer. The method 700 can also, optionally, involve depositing a contact metallization layer (e.g., electrical contact metallization layers 444 and 448) over exposed locations (e.g., electrode contact pad 432b) in the electrode material layers. The contact metallization layer material can be the same material or a different material than the material used for the conductive material layer.

The method 700 also involves forming or creating a cavity (step 736) through a portion of the microfabricated device. For example, with respect to FIG. 4, step 736 involves forming cavity 452 through the handle layer 404 and the first silicon oxide layer 408 to exposing the silicon layer 416, thereby forming the membrane 482. In one embodiment, the cavity is created by protecting the opposing side of the device and then using a deep reactive ion etch (DRIE) process.

The method 700 also involves etching a portion of the first oxide material layer (step 740) to create an undercut between the silicon layer (silicon layer 416) and the silicon wafer (handle wafer 404), similarly as described herein with respect to, for example, FIG. 4. The method 700 also involves dicing the wafer (step 644) produced by the previous steps to produce individual devices/chips.

Figure 8:
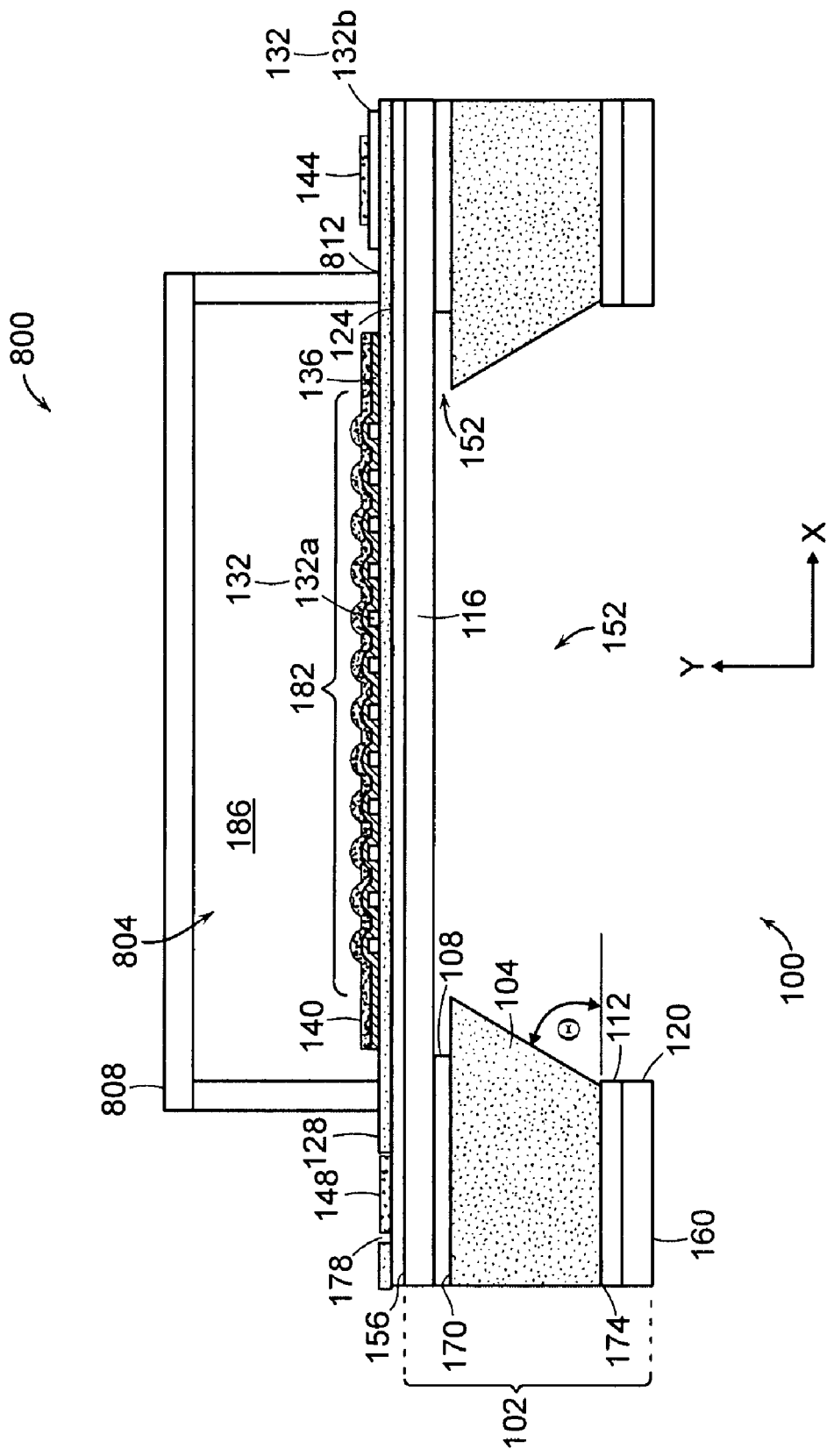
FIG. 8 is a schematic illustration of a microfabricated device and fluid channel, according to an illustrative embodiment of the invention.

FIG. 8 is a schematic illustration of a portion of an assay measurement system 800 that includes a microfabricated device (the device 100 of FIG. 1) and a fluid channel 804 used to direct a fluid in the region 186 to the surface of the device (for example, a surface of the conductive material layer 140). The channel 804 is formed by a cap structure 808 that is located over the device 100. A seal 812 (e.g., gasket) located between the cap structure 808 and the piezoelectric material layer 128 maintains a fluid seal such that fluid is retained in the region 186 (or, fluid flowing through region 186 is does not leak from the fluid channel 804).

Variations, modifications, and other implementations of what is described herein will occur to those of ordinary skill in the art without departing from the spirit and the scope of the invention and are considered to be encompassed thereby. Accordingly, the invention is not to be defined only by the preceding illustrative description.

What is claimed is:

1. A microfabricated device for operation in a fluid, comprising:
    a substrate having a first and second surface;
    a first electrode material layer located over the first surface of the substrate;
    a piezoelectric material layer located over the first electrode material layer;
    a second electrode material layer located over the piezoelectric material layer; and
    a layer of isolation material located over the second electrode material layer that at least one of chemically or electrically isolates a portion of the second electrode material layer from a fluid.

2. The microfabricated device of claim 1, comprising a layer of conductive material located over the layer of isolation material.

3. The microfabricated device of claim 2, wherein electrical potential of the layer of conductive material is controlled to reduce the electrical interaction between the microfabricated device and the fluid or a substance in the fluid.

4. The microfabricated device of claim 1, comprising a layer of immobilization material located over the layer of isolation material to facilitate immobilization of a substance on the microfabricated device.

5. The microfabricated device of claim 1, wherein the substrate comprises a silicon layer having a first and second surface, a first silicon oxide layer adjacent the first surface of the silicon layer, a second silicon oxide layer adjacent the second surface of the silicon layer, a first silicon nitride layer adjacent the first silicon oxide layer having a surface that is the first surface of the substrate, and a second silicon nitride layer adjacent the second silicon oxide layer.

6. The microfabricated device of claim 1, wherein the second electrode material layer is a layer of metal or semiconductor material.

7. The microfabricated device of claim 5, wherein a cavity is formed in the second silicon nitride layer, the second silicon oxide layer and the silicon layer exposing the first silicon nitride layer and a portion of the silicon oxide layer between the silicon layer and the first silicon nitride layer is removed to form an undercut.

8. The microfabricated device of claim 1, wherein the isolation material is an oxide material.

9. The microfabricated device of claim 1, wherein the first or second electrode material layer comprises one or more electrodes.

10. The microfabricated device of claim 9, wherein the one or more electrodes comprise a pair of sensing electrodes and a pair of actuation electrodes.

11. The microfabricated device of claim 9, wherein the first or second electrode material layer comprises an interdigitated sensing electrode pair and an interdigitated actuation electrode pair.

12. The microfabricated device of claim 11, wherein the microfabricated device is a flexural plate wave device.

13. The microfabricated device of claim 1, comprising a layer of conductive material located over the layer of isolation material to facilitate immobilization of a substance on the microfabricated device.

14. The microfabricated device of claim 13, wherein electrical potential of the layer of conductive material is controlled to reduce the electrical interaction between the microfabricated device and the fluid or a substance in the fluid.

15. The microfabricated device of claim 3, wherein the substance is selected from the group consisting of whole cells, bacteria, yeast, fungi, blood cells, dissociated tissue cells, spores, viruses, proteins, antibodies, lipids, carbohydrates, nucleic acids, peptides and small molecules.

16. The microfabricated device of claim 2, wherein the layer of conductive material is a barrier between the layer of isolation material and the fluid.

17. The microfabricated device of claim 1, comprising a fluid channel over the layer of isolation material to deliver the fluid to a surface of the layer of isolation material.

18. The microfabricated device of claim 17, wherein a signal output by the first and second electrode material layers is representative of the propagation characteristics of a structure incorporates the piezoelectric material layer.

19. A microfabricated device for operation in a fluid, comprising:
    a substrate having a first and second surface;
    a first electrode material layer located over the first surface of the substrate;
    a piezoelectric material layer located over the first electrode material layer;
    a second electrode material layer located over the piezoelectric material layer; and
    a layer of isolation material located over the second electrode material layer that at least one of chemically or electrically isolates a portion of the second electrode material layer from a fluid,
    wherein the first or second electrode material layer comprises a pair of sensing electrodes and a pair of actuation electrodes.

* * * * *